United States Patent [19]

Bell

[11] Patent Number: 5,672,342
[45] Date of Patent: Sep. 30, 1997

[54] ANIMAL SCENT ATTRACTANT KITS AND METHODS

[76] Inventor: Donald G. Bell, P.O. Box 548, Atmore, Ala. 36504

[21] Appl. No.: 390,757

[22] Filed: Feb. 17, 1995

[51] Int. Cl.$^6$ ............................ A01N 25/00; A01N 31/06
[52] U.S. Cl. .................................... 417/84; 43/1; 222/175
[58] Field of Search ...................... 43/1; 424/84; 222/175

[56] References Cited

U.S. PATENT DOCUMENTS

| | | |
|---|---|---|
| 4,944,940 | 7/1990 | Christenson, II ............... 424/84 |
| 5,010,851 | 4/1991 | Gvaryahu et al. ............... 119/174 |
| 5,369,903 | 12/1994 | Cox ...................................... 43/1 |

*Primary Examiner*—Terressa Mosley
*Attorney, Agent, or Firm*—Edward M. Livingston, Esq.

[57] ABSTRACT

Animal scent attractant and cover scent kits made from urine collected from a single animal and packaged for storage prior to use. The method of making the kits involves placing a single animal into a staging stall under controlled conditions wherein urine is collected. A series of primary and secondary staging stalls may be used to enhance urine production. Such stalls preferably have solid floors made from concrete, wood or stainless steel which may contain a covered trough to direct the urine into a bottle for collection. Heat and music may also be provided to the stall to enhance urine production, depending on the species of animal.

17 Claims, No Drawings

ANIMAL SCENT ATTRACTANT KITS AND METHODS

BACKGROUND OF THE INVENTION

This invention relates to animal scent attractants, and more particularly animal scent attractants used to cover a human's scent and provide a lure for use in hunting or photographing animals, such as deer, fox, raccoon and other wildlife.

Hunting wild animals, especially deer, requires a blend of patience, intelligence, endurance and the right equipment. Animals rely on their highly developed sense of smell to alert them of a great number of elements which may affect them, such as food, danger and the presence of other animals, thus requiring a hunter to blend into the surroundings to evade detection by these animals. Attracting the animals to an area a hunter or photographer has selected are also of much importance.

With regard to deer, especially a buck (male deer), a lure or cover scent are used to attract and evade detection. Such scents are commonly used by photographers and wildlife enthusiasts, as well as hunters.

Primarily, the lures for attracting buck deer are made from urine extracted from doe in estrous (in heat) and dominant bucks. Such lures are used to deceive the deer, especially the dominant buck, by bringing it closer to a specific area so designated by the user. Other animal lures are also made from urine taken from the animals.

Masking the human scent is imperative for a lure to work properly. Such masking is accomplished by a number of methods, specifically, by use of cover scents in the animal category. Cover scents are made from animal urine which are used to mask human odor by applying the urine to a drag line attached to the person and allowing it to contact the ground, leaving a trail of animal scent, thus masking the human odor.

In the prior art, the predominant type of deer lures and animal cover scents are of urine collected from a number of animals and stored in bulk containers until needed. Such deer lures are a blend of many animals due to the method by which it is collected.

The main problem associated with the prior art is that the resulting lures are a blend of urine from many animals, thus emitting an odor characteristic of a group of deer or animals. These lures made from blended urine must also be preserved to keep the product at peak levels of performance. Furthermore, because the lure made from blended urine is not as effective, it must be enhanced by the inclusion of a gland of the animal, such as a tarsal or interdigital gland, in the case of a deer. An example of such a prior art lure is shown in U.S. Pat. No. 4,944,940, issued Jul. 31, 1990 to Christenson, II.

In the case of deer, the afore-mentioned problem is especially evident. Young buck deer are gregarious and lures tend to attract these deer specifically because of the blend of urine from many deer. On the other hand, mature buck deer, which are of most interest to hunters, are territorial and battle among themselves to establish territorial lines. The most dominant of these bucks establish their territory with a scrape line, or outline of an area, and thus, force less powerful bucks to concede to less desirable areas. Unfortunately, the lures of the prior art tend to confuse the dominant buck into the perception that there are many deer in its territory which it thus avoids.

Contrary to the animal lures in the prior art, the present invention is a lure made from the urine of a single animal, specially collected and bottled without requiring the insertion of a gland or even a preservative for enhancement. Thus, a deer lure made from the present invention can attract desirable mature buck deer by its mere introduction into a territory.

SUMMARY OF THE INVENTION

The primary object of the present invention is to provide a animal scent attractant kit which effectively lures desirable animals to a location chosen by the user.

Another object of the present invention is to provide a deer lure scent and animal cover scent which will overcome the problem of prior art deer lures and animal cover scents of confusing and imitating deer herds or multiple animals.

A further object of the present invention is to provide animal cover scents that will prevent the illusion that a single individual animal has tracked through or is in a specific area.

As related to deer, a specific object of the invention is to establish a buck lure that will present the buck with the illusion of another single, individual dominant buck entering or having penetrated its territory.

A further specific object related to deer is to provide a buck lure that will present the buck with the illusion that a single individual doe or doe in estrous is in its territory.

An even further object related specifically to deer is to establish a buck lure that will present the buck with the illusion that another single individual dominant buck in rut has penetrated its territory.

The present invention fulfills the above and other objects by providing an animal scent attractant kit made from the urine from a single animal which is stored in a sealed bottle until needed for use. The urine may be mixed with a preservative to extend shelf and use life, but such is not necessary. The invention covers the method of making the animal scent attractant kit which may vary but generally involves placing a single animal into a stall during which time the animal is fed and watered. Whenever the animal urinates, the urine is collected immediately after it is voided and then it is packaged. Prior to packaging, the urine may be mixed with a preservative selected from a group of well known preservatives. The urine is generally packaged into a bottle which contains a cover that can be sealed in wax. The bottle may be refrigerated as necessary until shipped. The stalls in which the urine is collected may contain floors which are elevated, sunken and/or grated, the floors being made of concrete, wood, stainless steel or other similar materials. Each stall may also have walls that are made of wire, wood or stainless steel. The bottom of the stalls may contain a covered trough which directs the urine immediately after it is voided into the packing bottles. Although the urine may be collected at one time, for better production a series of stalls may be used. After a first stall, what is called a primary staging stall, a second stall may be used in which the animal voids any further urine for collection before the animal is released to wait until the next cycle. The stalls used to collect the urine may be heated or may even have piped in music in order to enhance production of urine. The particular animals with which this method may be employed include nearly every form of wildlife, but more commonly deer, fox and raccoon.

The above and other objects, features and advantages of the present invention will become even more readily apparent to those skilled in the art upon a reading of the following detailed description of the preferred embodiments.

DETAILED DESCRIPTION OF THE PREFERRED EMBODIMENTS

The present invention is specifically directed to animal scent attractant and cover kits and methods of making same using the urine from a single animal. Each of the scents in the kit, whether it be from a deer, such as a doe or doe in estrous or dominant buck, or other animal, emits a scent characteristic to each individual animal.

Each particular animal scent attractant or cover kit is collected and packaged by a well-controlled method to insure its effectiveness. The animal urine is packaged in a single bottle with a cover which may be sealed in wax. Prior to packaging, the urine may be mixed with a preservative selected from a group consisting of glycerine, propylene, glycol, mineral oil, alcohol and bandac. Even though preservatives are not necessary, it may comprise 0.1% of the overall animal scent attractant kit.

The method employed by the present invention for making the animal scent attractant kit has many variations, but the three primary steps involve placing an animal into a stall during which time the animal is fed and watered. During the period of time the animal is in the stall, whenever the animal urinates, its urine is collected as it is voided and then packaged. Prior to packaging the urine may be mixed with a preservative and/or refrigerated until shipped, even though preservative is not necessary.

The method of collecting the urine may be done in two stages, first in a primary staging stall wherein the feeding and watering takes place and thereafter in a secondary stall. The stalls are generally covered to protect the animals from the weather and generally have a hard floor, such as concrete, wood or stainless steel. To enhance production of urine, the stalls may be heated and may even have music piped into the stall. It has been shown through experimentation that various types of music enhance the production of urine, depending on the type of animal.

The manufacture of the animal attractant kit has been particularly successful using the above-described method with deer, even though it can be employed to fox, raccoons and other animals as well. With regard to a buck lure, the lures have provided an animal scent attractant wherein a large buck will sense a single individual doe, doe in estrous or another dominant buck in its territory. When using the present invention, the buck is not confused with blended lures or lures using a lot of preservatives and the buck more strongly senses that another single individual deer has entered its territory which it must defend. Thus, the buck will more likely overlook its natural sense of caution and be drawn to a particular area desired by a hunter or photographer. If the animal scent attractant is made from a doe or a doe in estrous, the buck will sense a single individual doe in its territory, causing it to investigate.

The animal scent attractant kit of this invention also works as an animal cover scent that helps to mask the human odor when it is applied to a drag line attached to the individual.

Thus, the present invention provides a novel animal scent attractant and cover kit and method for making same that has proven very successful in use by hunters, photographers or wildlife enthusiasts.

Although only some animal scent attractant kits and methods have been described in detail hereinabove, all improvements and modifications to this invention within the scope or equivalents of the claims are included in this invention.

Having thus described my invention, I claim:

1. An animal scent attractant and cover scent comprising animal urine collected from a single individual animal at a given time of the same type of animal which said attractant and cover scent is designed to attract, said urine being packaged after urination.

2. The animal scent attractant and cover scent of claim 1 wherein the animal urine is packaged in a single bottle having a cover placed thereon which is sealed in wax.

3. The animal scent attractant and cover scent of claim 1 or 2 wherein the urine is mixed with a preservative comprising 0.1% of the scent.

4. The animal scent attractant and cover scent of claim 3 wherein the preservative is selected from a group consisting of glycerine, propylene, glycol, mineral oil, alcohol and bandac.

5. The animal attractant and cover scent of claim 1 or 2 further comprising a gland taken from an animal of a same species and packaged together with the urine.

6. The animal scent attractant and cover scent of claim 1 wherein the animal is a deer.

7. The animal scent attractant and cover scent of claim 1 wherein the animal is a fox.

8. The animal scent attractant and cover scent of claim 1 wherein the animal is a raccoon.

9. A method of making an animal scent attractant and cover scent comprising:
placing a single individual animal at a given time into a stall during which time the animal is fed and watered;
collecting the urine from the animal as it is voided; and
packaging the urine from the single animal.

10. The method of claim 9 further comprising releasing the animal from the stall and placing the animal into a second stall wherein the steps of collecting and packaging the urine are repeated.

11. The method of claim 9 or 10 further comprising mixing the collected urine with a preservative prior to packaging.

12. The method of claim 9 or 10 further comprising refrigerating the packaged urine until it is shipped.

13. The method of claim 9 wherein either or both stalls are covered.

14. The method of claim 10 wherein either or both stalls are covered.

15. The method of claim 9, 10 or 14 wherein the stalls have a floor which is made of concrete.

16. The method of claim 9, 10 or 14 wherein the stalls have a floor which is made of wood.

17. The method of claim 9, 10 or 14 wherein the stalls have a floor which is made of stainless steel.

* * * * *